United States Patent [19]

Regnat et al.

[11] Patent Number: 5,298,644
[45] Date of Patent: Mar. 29, 1994

[54] ARYL PHOSPHINITES

[75] Inventors: Dieter Regnat, Frankfurt am Main; Hans-Jerg Kleiner, Kronberg/Ts, both of Fed. Rep. of Germany

[73] Assignee: Hoechst Aktiengesellschaft, Frankfurt am Main, Fed. Rep. of Germany

[21] Appl. No.: 64,259

[22] Filed: May 19, 1993

[30] Foreign Application Priority Data

May 21, 1992 [DE] Fed. Rep. of Germany ....... 4216882

[51] Int. Cl.$^5$ .............................................. C07F 9/28
[52] U.S. Cl. ...................................... 558/70; 558/190; 558/197
[58] Field of Search ........................................... 558/70

[56] References Cited

PUBLICATIONS

Muller, E., *Houben-Weyl*, "Methoden der organischen Chemie": vol 12, Stuttgart, Georg Thieme Verlag, 1963, pp. 210–211.

*Primary Examiner*—Mary C. Lee
*Assistant Examiner*—Michael G. Ambrose

[57] ABSTRACT

Aryl phosphinites of the formula (I)

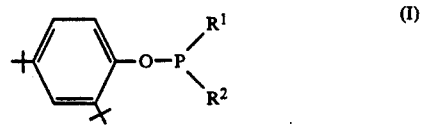

can be prepared in a simple manner and in high yields by reacting 2,4-di-tert.-butylphenylphosphonous dihalides with alkyl- or arylmagnesium bromides or alkyl- or arylmagnesium chlorides.

Aryl phosphinites serve for the preparation of secondary phosphine oxides which are used as starting materials for the preparation of phosphine ligands in catalyst systems.

7 Claims, No Drawings

ARYL PHOSPHINITES

The present invention relates to novel aryl dialkyl- and alkylaryl-phosphinites and to a process for their preparation.

Aryl dialkyl- and alkylaryl-phosphinites are industrially valuable compounds which are used, for example, as starting materials for the synthesis of secondary phosphine oxides, which are used as starting materials for phosphine ligands in catalyst systems.

Phosphinous esters can be prepared from phosphinous halides by reaction with phenol. However, phosphinous halides are difficult to obtain industrially. In practice, the only industrially available precursor is diphenylphosphinous chloride.

When phosphinous esters are prepared by reaction of dichlorophosphorous ester and Grignard reagents, a yield-reducing side reaction takes place exchanging the alcoholate radical OR for the Grignard compound, so that even in the most favorable cases the yield obtained does not exceed 60 % (Houben-Weyl, K. Sasse, Vol. 12/1, p. 210).

Moreover, there has been a prejudice in the literature concerning the reaction of dihalophosphorous esters with organomagnesium bromides, which was believed first always to result in insoluble complex compounds which first have to be separated into their components by addition of further auxiliaries, for example pyridine, in order to enable isolation of the desired phosphinous esters.

Accordingly, the object of the present invention was to obtain aryl dialkyl- and alkylaryl-phosphinites in a simple manner and the highest possible yields.

It has now been found that 2,4-di-tert.-butylphenyl dialkyl- and alkylaryl-phosphinites can surprisingly be prepared in high yields by reaction of a 2,4-di-tert.-butylphenylphosphonous dihalide with alkyl- or arylmagnesium bromides or alkyl- or arylmagnesium chlorides, halide likewise being chloride or bromide.

The invention relates to 2,4-di-tert.-butylphenyl dialkyl- and alkylaryl-phosphinites of the formula I,

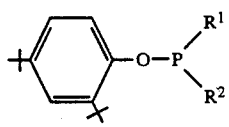

(I)

in which $R^1$ and $R^2$, independently of one another, are each a branched, unbranched or cyclic alkyl radical having 1 to 20 carbon atoms, or $R^1$ is one of the alkyl radicals defined above and $R^2$ is a phenyl or naphthyl radical, each of which is unsubstituted or carries 1 to 5 substituents, the substituents being identical or different and a non-aromatic $C_1$-$C_{12}$-hydrocarbon radical, a $C_1$-$C_{12}$-alkoxy radical, $C_1$-$C_{12}$alkylthio radical, di-$C_1$-$C_{12}$-alkylamino radical or an aryl radical or aryloxy radical each having 6 to 12 carbon atoms.

For the purposes of the invention, preference is given to compounds of the formula (I) in which $R^1$ and $R^2$, independently of one another, are each a branched or unbranched alkyl radical having 1 to 10, preferably 2 to 6, carbon atoms or a cyclic alkyl radical having 6 to 12, preferably 6 to 7, carbon atoms.

For the purposes of the invention, preference is also given to compounds of the formula (I) in which $R^1$ is a branched or unbranched alkyl radical having 1 to 10, preferably 2 to 6. carbon atoms or a cyclic alkyl radical having 6 to 12, preferably 6 to 7, carbon atoms and $R^2$ is a phenyl radical which is substituted by 1 to 3 $C_1$-$C_8$-alkyl radicals, $C_1$-$C_8$-alkoxy radicals, $C_1$-$C_8$-alkylthio radicals, di-$C_1$-$C_8$-alkylamino radicals, phenyl radicals or phenoxy radicals, an unsubstituted naphthyl radical or a naphthyl radical which is substituted by 1 to 3 $C_1$-$C_8$-alkyl radicals, $C_1$-$C_8$-alkoxy radicals, $C_1$-$C_8$-alkylthio radicals, di-$C_1$-$C_8$-alkylamino radicals, phenyl radicals or phenoxy radicals.

Of particular interest are compounds of the formula (I) in which $R^1$ and $R^2$, independently of one another, are each methyl, ethyl, propyl, butyl or cyclohexyl.

Of particular interest are also compounds of the formula (I) in which $R^1$ is methyl, ethyl, propyl, butyl or cyclohexyl and $R^2$ is a tolyl, xylyl, mesityl, 2,4,5-trimethylphenyl, 2,4,6-tri-tert.-butylphenyl, 2,4-di-tert.-octylphenyl, biphenyl, naphthyl, methylnaphthyl, dimethylnaphthyl or trimethylnaphthyl radical.

Of particular interest are the following compounds of the formula (I):

2,4-di-tert.-butylphenyl dimethylphosphinite,
2,4-di-tert.-butylphenyl diethylphosphinite,
2,4-di-tert.-butylphenyl dipropylphosphinite,
2,4-di-tert.-butylphenyl diisopropylphosphinite,
2,4-di-tert.-butylphenyl dibutylphosphinite,
2,4-di-tert.-butylphenyl di(1-methylpropyl)phosphinite,
2,4-di-tert.-butylphenyl di(2-methylpropyl)phosphinite,
2,4-di-tert.-butylphenyl dicyclohexylphosphinite,
2,4-di-tert.-butylphenyl 2,4,6-trimethylphenylisopropylphosphinite,
2,4-di-tert.-butylphenyl 2,4,6-trimethylphenyl(2-methylpropyl)phosphinite,
2,4-di-tert.-butylphenyl 2,4,6-trimethylphenylcyclohexylphosphinite,
2,4-di-tert.-butylphenyl 1-naphthyl (isopropyl) phosphinite,
2,4-di-tert.-butylpheny.U-naphthyl(2-methylpropyl)-phosphinite and
2,4-di-tert.-butylphenyl 1-naphthyl (cyclohexyl) phosphinite.

The invention also relates to a process for the preparation of the 2,4-di-tert.-butylphenyl phosphinites of the formula (I) in which $R^1$ and $R 2$ have the abovementioned meanings, which comprises a) in the case where $R^1$ and $R 2$ are different from one another, first reacting, in a first step, a 2,4-di-tert.-butylphenylphosphonous dihalide with a Grignard compound of the formula $R^1$-MGX in a molar ratio of 0. 8: 1 to 1. 2: 1, preferably 1:1, $R^1$ having the abovementioned meanings, halide being chloride or bromide and X being a halogen having an atomic weight of at least 35, preferably chlorine or bromine, in particular bromine, to give a halophosphonous ester of the formula (II)

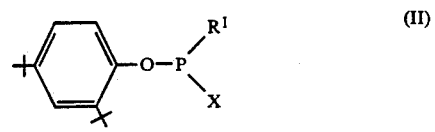

(II)

and then reacting, in a second step, the compound of the formula (II) with a Grignard compound of the formula $R^2$-MgX in a molar ratio of 0.8:1 to 1.2:1, preferably 1:1, $R^2$ having one of the abovementioned meanings other than $R^1$, b) in the case where $R^1$ and $R^2$ have the same meaning, reacting a 2,4-di-tert.-butylphenylphosphonous dihalide with a Grignard compound $R^1$-MGX in a molar ratio of 0.8:2 to 1.2:2, preferably 1:2.

Preparation of the Grignard compounds $R^1$-MGX or $R^2$-MgX is carried out in a manner known per se by reacting a hydrocarbyl halide $R^1$-X or $R^2$-X under Grignard conditions, advantageously with intimate mixing, with an at least stoichiometric amount of finely divided magnesium and, preferably, in an aprotic, organic solvent, for example an ether, in particular diethyl ether, dipropyl ether or diisopropyl ether, ethylene glycol dimethyl ether, ethylene glycol diethyl ether, diethylene glycol dimethyl ether, diethylene glycol diethyl ether or methyl tert.-butyl ether, dioxane or tetrahydrofuran. Since Grignard compounds are sensitive to hydrolysis and oxidation, it may be advantageous to carry out the reaction under an inert gas atmosphere. However, such a procedure is not at all necessary for successful completion of the reaction. Suitable inert gases are nitrogen or argon. The reaction temperature is in general between 20° and 125° C., but preferably between 30° and 70° C. It may be advantageous to provide good turbulence during the Grignard reaction, for example by applying ultrasound.

The hydrocarbon halide $R^1$-X preferably used for the first reaction step of process variant a) is one in which $R^1$ is a phenyl radical substituted by at least one of the abovementioned substituents, one substituent preferably being in the 2-position, or is a naphthyl radical which is unsubstituted or substituted by at least one of the abovementioned substituents.

It may be advantageous for the preparation of the compound of the formula (II) to add the solution or suspension of the Grignard compound $R^1$-MGX to a solution of 2,4-di-tert.-butylphenylphosphonous dihalide in small portions or continuously with vigorous mixing, advantageously at a temperature below 0° C.

For preparing the compounds of the formula (I) in variant b) and in the second step of variant a), the reactants can be combined with one another as desired. However, it is technically advantageous to add the 2,4-di-tert.-butylphenylphosphonous dihalide in variant b) or the compound of the formula (II) in the second step of variant a) to the solution or suspension of the corresponding Grignard compound in small portions or continuously if the radicals $R^1$ and $R^2$ have the abovementioned meanings with the exception of primary alkyl groups.

In the case where $R^1$ and $R^2$ are primary alkyl groups, it is advantageous to add the solution or suspension of the Grignard compound in variant b) to a solution of 2,4-di-tert.-butylphenylphosphonous dihalide or, in the second step of variant a), to the solution of the compound of the formula (II) with vigorous mixing, advantageously at a temperature below 0° C.

Suitable diluents for the first and second step of variant a) and for variant b) are inert, aprotic solvents, for example an aliphatic hydrocarbon fraction, hexane, cyclohexane, methylcyclohexane, toluene, xylenes or one of the abovementioned ethers or mixtures of these solvents. The reaction temperature in these reaction steps is between −30° and +50° C., but preferably between −20° and +20° C. As a rule, the reactions are exothermic; accordingly, it may be advantageous to control the course of the reaction by cooling. The most favorable results are obtained by using the reactants in stoichiometric amounts. However, it is also possible to use one reactant in excess; however, in general, no specific advantages are obtained by this. Advantageously, the reaction mixture is stirred until reaction is complete and the precipitated magnesium halide is then separated off. The solvents can be removed from the filtrate in the usual manner, advantageously by distillation, in particular under reduced pressure.

The compounds of the formula (I) can be isolated from the crude products by customary methods, for example by distillation or crystallization.

The present invention furthermore relates to the use of the aryl dialkyl- and alkylaryl-phosphinites according to the invention as starting materials for the preparation of secondary phosphine oxides by hydrolysis in water or an aqueous-organic medium. Purification of the starting materials for the purpose mentioned is not necessary. Secondary phosphine oxides are intermediates for the preparation of flame retardants, metal extractants and starting materials for the preparation of tertiary phosphine oxides, whose deoxygenation leads to tertiary phosphines which can be used in various ways as catalysts.

EXAMPLES

In the Examples which follow, the compounds according to the invention of the formula (I) were prepared by process variants a) or b) listed below:

Process Variant a)

The corresponding Grignard compound $R^1$-MgBr was prepared from 150 mmol of the organobromine compound $R^1$-Br and 150 mmol (3.65 g) of magnesium turnings in 90 ml of tetrahydrofuran under a nitrogen atmosphere and with the exclusion of moisture. The resulting solution or suspension of the organometallic compound was then metered to a solution of 150 mmol (46.1 g) of 2t4-di-tert.-butylphenylphosphonous dichloride in 120 ml of tetrahydrofuran/n-heptane (1:1) over a period of 30 to 40 minutes with vigorous stirring at a temperature of −20° to −10° C. The reaction mixture was then allowed to warm to about 20° C., and stirring was continued for another 3 hours to complete the reaction. The corresponding Grignard compound $R^2$-MgBr was prepared from 150 mmol of the organobromine compound R Br and 150 mmol (3.65 g) of magnesium turnings in 90 ml of tetrahydrofuran under a nitrogen atmosphere and with the exclusion of moisture. The resulting solution or suspension of the organometallic compound was then metered to the previously prepared 2,4-di-tert.-butylphenylphosphinous chloride over a period of 30 to 40 minutes with vigorous stirring at a temperature of −20° to −10° C. The reaction mixture was then allowed to warm to about 20° C., and stirring was continued for another 3 hours to complete the reaction. After the precipitated magnesium salt had been filtered off and washed with about 50 ml of petroleum ether, the solvent was distilled off first at about 0.02 bar and then in a high vacuum, giving colorless or yellow oils which, if desired, were distilled in a high vacuum.

Process Variant b)

The corresponding Grignard compound was prepared from 300 mmol of organobromine compound and 300 mmol (7.3 g) of magnesium turnings in 180 ml of tetrahydrofuran under a nitrogen atmosphere and with the exclusion of moisture. The resulting solution or suspension of the organometallic compound was then metered to a solution of 150 mmol (46.1 g) of 2,4-di-tert.-butylphenylphosphonous dichloride in 120 ml of tetrahydrofuran/n-heptane (1:1) over a period of 30 to 40 minutes with vigorous stirring at a temperature of −20° to −10° C. The reaction mixture was then allowed to warm to about 20° C., and stirring was continued for another 3 hours to complete the reaction. After the precipitated magnesium salt had been filtered off and washed with about 50 ml of petroleum ether, the solvent was distilled off first at about 0.02 bar and then in a high vacuum, giving colorless or yellow oils which, if desired, were distilled in a high vacuum. The yield of the compounds according to the invention was determined in each case by $^{31}$P NMR spectroscopy and was in general between 70 and 90%. In the cases mentioned, distillation was carried out to characterize the product.

1) 2,4-Di-tert.-butylphenyl Dimethylphosphinite (by Variant b)

15.2 g (300 mmol) of chloromethane as the starting material gave 40 g of a yellow oil having a 2,4-di-tert.-butylphenyl dimethylphosphinite content of 75%.

$^{31}$P NMR: $\delta_{[D]-chloroform} = 117.4$ ppm

2) 2,4-Di-tert.-butylphenyl Diethylphosphinite (by Variant b)

32.70 g (300 mmol) of bromoethane as the starting material gave 41 g of a pale yellow oil having a 2,4-tert.-butylphenyl diethylphosphinite content of 79%.

$^{31}$P NMR: $\delta_{[D]-chloroform} = 130.8$ ppm

3) 2,4-Di-tert.-butylphenyl Dipropylphosphinite (by Variant b)

36.90 g (300 mmol) of 1-bromopropane as the starting material gave 48 g of a pale yellow oil having a 2,4-di-tert.-butylphenyl dipropylphosphinite content of 83%.

$^{31}$P NMR: $\delta_{[D]-chloroform} = 125.4$ ppm

4) 2,4-Di-tert.-butylphenyl Diisopropylphosphinite (by Variant b)

The Grignard compound was prepared starting with 36.90 g (300 mmol) of 2-bromopropane. The general process variant b) was followed, except that the 2,4-di-tert.-butyl-phenylphosphonous dichloride was added to the suspension of the Grignard compound, giving 48 g of a pale yellow oil having a 2,4-di-tert.-butylphenyl diisopropylphosphinite content of 90-95 %.

$^{31}$P NMR: $\delta_{[D]-chloroform} = 137.9$ ppm. Distillation at 0.4 to 0.5 mbar gave 43.2 g (90 %) of the above compound as a colorless oil having a boiling point of 136° C.

2,4-Di-tert.-butylphenyl Dibutylphosphinite (by Variant b)

41.10 g (300 mmol) of 1-bromobutane as starting material gave 52 g of a pale yellow oil having a 2,4,di-tert.-butylphenyl dibutylphosphinite content of 71%.

$^{31}$P NMR: $\delta_{[D]-chloroform} = 126.5$ ppm

6) 2,4-Di-tert.-butylphenyl Di(1-methylpropyl)phosphinite (by Variant b)

The Grignard compound was prepared starting with 41.10 g (300 mmol) of 2-bromobutane. The general process variant b) was followed, except that the 2,4-di-tert.-butyl-phenylphosphonous dichloride was metered to the suspension of the Grignard compound, giving 51.5 g of a pale yellow oil having a 2,4-di-tert.-butylphenyl di(1-methylpropyl)phosphinite content of 75%.

$^{31}$P NMR: $\delta_{[D]-chloroform} = 120-140$ ppm, broad. Distillation at 0.4 to 0.5 mbar gave 34.5 g (67%) of the above compound as a colorless oil having a boiling point of 154°0 to 156° C.

7) 2,4-Di-tert.-butylphenyl Di(2-methylpropyl)phosphinite (by Variant b)

The Grignard compound was prepared starting with 41.10 g of 1-bromo-2-methylpropane. The general process variant b) was followed, except that the 2,4-di-tert.-butyl-phenylphosphonous dichloride was metered to the suspension of the Grignard compound, giving 52 g of a pale yellow oil having a 2,4-di-tert.-butylphenyl di(2-methylpropyl)phosphinite content of 70%.

$^{31}$P NMR: $\delta_{[D]-chloroform} = 121.8$ ppm,, broad. Distillation at 0.4 to 0.5 mbar gave 35.3 g (68 %) of the above compound as a colorless oil having a boiling point of 144° to 146°0 C.

8) 2,4-Di-tert.-butylphenyl Dicyclohexylphosphinite (by Variant b)

The Grignard compound was prepared starting with 48.12 g (300 mmol) of bromocyclohexane. The general process variant b) was followed, except that 2,4-di-tert.-butyl-phenylphosphonous dichloride was metered to the suspension of the Grignard compound, giving 60 g of a yellow oil having a 2,4-di-tert.-butylphenyl dicyclohexylphosphinite content of 71%.

$^{31}$P NMR: $\delta_{[D]-chloroform} = 133.3$ ppm

9) 2,4-Di-tert.-butylphenyl 2,4,6-trimethylphenylisopropylphosphinite (by Variant a)

29.87 g (150 mmol) of 1-bromo-2,4,6-trimethylbenzene and 18.45 g (150 mmol) of isopropyl bromide as the starting materials gave 59 g of a yellow oil having a 2,4-di-tert.-butylphenyl 2,4,6-trimethylphenylisopropylphosphinite content of 70%.

$^{31}$P NMR: $\delta_{[D]-chloroform} = 129.0$ ppm

10) 2,4,Di-tert.-butylphenyl 2,4,6-trimethylphenyl-2-methylpropylphosphinite (by Variant a)

29.87 g (150 mmol) of 1-bromo-2,4,6-trimethylbenzene and 20.55 g (150 mmol) of 2-methylbromopropane as the starting materials gave 61.5 g of a yellow oil having a 2,4-di-tert.-butylphenyl 214;6-trimethylphenyl-2-methylpropylphosphinite content of 76%.

$^{31}$P NMR: $\delta_{[D]-chloroform} = 121.9$ ppm

11) 2,4-Di-tert.-butylphenyl 2,4,6-trimethylphenylcyclohexylphosphinite (by Variant a)

29.87 g (150 mmol) of 1-bromo-2,4,6-trimethylbenzene and 24.06 g (150 mmol) of bromocyclohexane as the starting materials gave a yellow oil having a 2,4-di-tert.-butylphenyl 2,4,6-trimethylphenylcyc lohexylphosphinite content of 67%.

12) 2,4-Di-tert.-butylphenyl 1-naphthylisopropylphosphinite (by Variant a)

31.05 g (150 mmol) of 1-bromonaphthalene and 18.45 g (150 mmol) of isopropyl bromide as the starting materials gave 60.5 g of a yellow oil having a 2,4-di-tert.-butylphenyl 1-naphthylisopropylphosphinite content of 89%.

$^{31}$P NMR: $\delta_{[D]\text{-chloroform}} = 117.1$ ppm

13) 2,4-Di-tert.-butylphenyl 1-naphthyl-2-methylpropylphosphinite (by Variant a)

31.05 g (150 mmol) of 1-bromonaphthalene and 20.55 g (150 mmol) of 2-methylbromopropane as the starting materials gave 63 g of a yellow oil having a 2,4-di-tert.-butylphenyl 1-naphthyl-2-methylpropylphosphinite content of 79%.

$^{31}$P NMR: $\delta_{[D]\text{-chloroform}} = 110.5$ ppm

14) 2,4-Di-tert.-butylphenyl 1-naphthylcyclohexylphosphinite (by Variant a)

31.05 g (150 mmol) of 1-bromonaphthalene and 24.06 g (150 mmol) of bromocyclohexane as the starting materials gave 66 g of a yellow oil having a 2.4-di-tert.-butylphenyl 1-naphthylcyclohexylphosphinite content of 75%.

$^{31}$P NMR: $\delta_{[D]\text{-chloroform}} = 115.0$ PPM

USE EXAMPLES

Synthesis of Secondary Phosphine Oxides

1 Diisopropylphosphine Oxide 32.3 g (0.1 mol) of 2,4-di-tert.-butylphenyl diisopropylphosphinite from Example 2 were reacted in 100 ml of acetonitrile with 2. 0 g (0. 11 mol) of water, and the mixture was then stirred at 70° C. for 1 hour. The solvent was distilled off in vacuo, 50 ml of water and 100 ml of ethyl acetate were added, the phases were separated, and the organic phase was extracted two more times with 50 ml each of water. The combined aqueous phases were evaporated, and the residue distilled in vacuo, giving 10.0 g (75%) of a colorless liquid having a boiling point of 40° to 42° C./0.25 mbar.

2) Dibutylphosphine Oxide 35 g (0.1 mol) of 2.4-di-tert.-butylphenyl dibutylphosphinite from Example 5 were reacted in 100 ml of acetonitrile with 2.0 g (0.11 mol) of water at 20° C., and the mixture was then stirred at 70° C. for 1 hour. The solvent was distilled off in vacuo, 50 ml of water and 100 ml of ethyl acetate were added, the phases were separated, and the organic phase was extracted two more times with 50 ml each of water. The combined aqueous phases were evaporated, and the residue distilled in vacuo, giving 10.2 g (70%) of a colorless liquid having a boiling point of 102° to 104° C./0.25 mbar.

What is claimed is:

1. A compound of the formula (I)

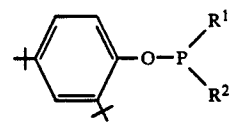

in which
R$^1$ and R$^2$, independently of one another, are each a branched, unbranched or cyclic alkyl radical having 1 to 20 carbon atoms, or
R$^1$ is one of the alkyl radicals defined above and
R$^2$ is a phenyl or naphthyl radical, each of which can be unsubstituted or carry 1 to 5 substituents, the substituents being identical or different and a non-aromatic C$_1$–C$_{12}$-hydrocarbon radical, a C$_1$–C$_{12}$-alkoxy radical, C$_1$–C$_{12}$-alkylthio radical, di-C$_1$–C$_{12}$-alkylamino radical or an aryl radical or aryloxy radical each having 6 to 12 carbon atoms.

2. A compound as claimed in claim 1, wherein R$^1$ and R$^2$, independently of one another, are each a branched or unbranched alkyl radical having 1 to 10 carbon atoms or a cyclic alkyl radical having 6 to 12 carbon atoms.

3. A compound as claimed in claim 1, wherein R$^1$ and R$^2$, independently of one another, are each a branched or unbranched alkyl radical having 2 to 6 carbon atoms or a cyclic alkyl radical having 6 to 7 carbon atoms.

4. A compound as claimed in claim 1, wherein
R$^1$ is a branched or unbranched alkyl radical having 1 to 10 carbon atoms or a cyclic alkyl radical having 6 to 12 carbon atoms and
R$^2$ is a phenyl radical which is substituted by 1 to 3 of the following radicals: C$_1$–C$_8$-alkyl, C$_1$–C$_8$alkoxy, C$_1$–C$_8$-alkylthio, di-C$_1$–C$_8$-alkylamino, phenyl or phenoxy, an unsubstituted naphthyl radical or a naphthyl radical which is substituted by 1 to 3 of the following radicals: C$_1$–C$_8$-alkyl, C$_1$–C$_8$-alkoxy, C$_1$–C$_8$-alkylthio, di-C$_1$–C$_8$-alkylthio, di-C$_1$–C$_8$-alkylamino, phenyl or phenoxy.

5. A compound as claimed in claim 4, wherein R$^1$ is a branched or unbranched alkyl radical having 2 to 6 carbon atoms or a cyclic alkyl radical having 6 to 7 carbon atoms.

6. A compound as claimed in claim 1, wherein R$^1$ and R$^2$, independently of one another, are each methyl, ethyl, propyl, butyl or cyclohexyl.

7. A compound as claimed in claim 1, wherein R$^1$ is methyl, ethyl, propyl, butyl or cyclohexyl and R$^2$ is a tolyl, xylyl, mesityl, 2,4,5-trimethylphenyl, 2,4,5-tri-tert.-butylphenyl, 2,4-di-tert.-octylphenyl, biphenyl, naphthyl, methylnaphthyl, dimethylnaphthyl or trimethylnaphthyl radical.

* * * * *